United States Patent
Tobias

(10) Patent No.: US 7,802,464 B2
(45) Date of Patent: Sep. 28, 2010

(54) FET-BASED GAS SENSOR SYSTEM

(75) Inventor: Peter Tobias, Minnetonka, MN (US)

(73) Assignee: Honeywell International Inc., Morristown, NJ (US)

( * ) Notice: Subject to any disclaimer, the term of this patent is extended or adjusted under 35 U.S.C. 154(b) by 286 days.

(21) Appl. No.: 11/923,449

(22) Filed: Oct. 24, 2007

(65) Prior Publication Data

US 2009/0108380 A1    Apr. 30, 2009

(51) Int. Cl.
*G01N 27/00* (2006.01)
*H01L 23/00* (2006.01)

(52) U.S. Cl. ...................... 73/31.06; 257/253
(58) Field of Classification Search ................ 257/414, 257/416, 252, 253; 73/31.06
See application file for complete search history.

(56) References Cited

U.S. PATENT DOCUMENTS

| | | | |
|---|---|---|---|
| 4,444,644 A | | 4/1984 | Hiramoto et al. |
| 4,505,799 A | | 3/1985 | Baxter |
| 4,761,639 A | * | 8/1988 | Pyke et al. ................. 73/23.2 |
| 4,816,118 A | | 3/1989 | Oyama et al. |
| 6,758,962 B1 | * | 7/2004 | Fitzgerald et al. ........... 205/783 |
| 6,929,728 B2 | * | 8/2005 | Frerichs ..................... 204/416 |
| 2005/0123442 A1 | | 6/2005 | Gu et al. |

OTHER PUBLICATIONS

Bergveld, "ISFET, Theory and Practice," IEEE Sensor Conference Toronto, pp. 1-26, Oct. 2003.
Design Ideas, Edited by Bill Travis, pp. 87, 88, 90, 92, 94, 96, May 1, 2003.
National Semiconductor Corporation, LM134/LM234/LM334 3—Terminal Adjustable Current Sources, 14 pages, Mar. 2005.

* cited by examiner

*Primary Examiner*—Lisa M Caputo
*Assistant Examiner*—Punam Roy
(74) *Attorney, Agent, or Firm*—Crompton Seager & Tufte LLC

(57) ABSTRACT

A sensor system for detection of gas with a modified ion selection FET. The FET may have a gate of low conductivity material for detection of a species in a fluid. A component such as a capacitor may be connected to an electrode of the FET, such as a source, in conjunction with the FET to reduce noise of the detection signal of the species. One or more current sources may provide a current through the FET, and through a resistor to provide a constant source-to-drain voltage. The system may have a bulk voltage selection of either that of a voltage approximately equal to the FET source voltage or greater than the FET source voltage. Also, a guard ring may be implemented in the FET for preventing leakage currents relative to the source or drain.

16 Claims, 6 Drawing Sheets

FET-BASED GAS SENSOR SYSTEM

BACKGROUND

The invention pertains to sensors and particularly to gas sensors. More particularly, the invention pertains to FET-type gas sensors.

SUMMARY

The invention is a FET-based gas sensor incorporating a filter connected directly to a FET element.

DESCRIPTION

Chemical sensors based on field-effect transistors (FETs) need an electronic circuit for a read-out that is connected to source (S), drain (D) and gate (G) of the transistor. In one approach, the drain-source voltage may be fixed and the drain-source current can be kept constant by regulating the source-gate voltage, which is measured as sensor signal (e.g., FIG. 1). In another approach, the FET may be operated in pinch-off where the influence of a drain-source voltage is small and a drain-source current that is kept constant can lead easily to a source-gate voltage as a suitable sensor signal (e.g., FIG. 4). There may be various circuits, which are not optimized for FET-based gas sensors that have gates with low conductivity, which can lead to noise in the sensor signal. The term "fluid" may refer to a gas or a liquid herein.

Instead of filtering noise out of the sensor signal from the circuit in a separate low-pass filter, it appears easier and more advantageous to add a circuit component at a certain point in the circuit. An example of such component may be significantly-sized capacitor (for instance, about 10 μF or greater in some designs). The component may instead be some other kind. This should not only give the expected low-pass filtered sensor signals, but also improve the stability of the sensor signal, because the stabilizing effect of the capacitance is applied closer to the noise source. In a way, the low-conductivity gate may have more time to regulate the drain-source current to a constant value, without needing such large voltage swings that manifest themselves as noise. Large voltage swings may also lead to a shift in the filtered sensor signal, if the transfer characteristic of the device is non-linear, and the shift would depend on the noise amplitude, making the interpretation of the filtered sensor signal difficult.

Figure 1:
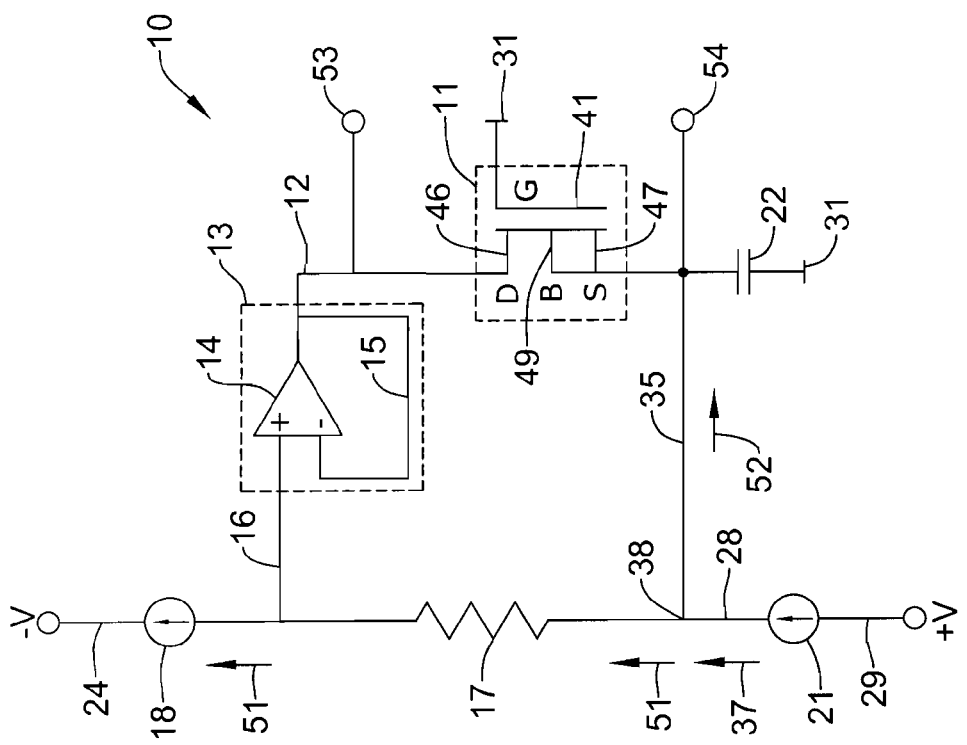
FIG. 1 is a diagram of a FET-based gas sensor.
Figure 2:
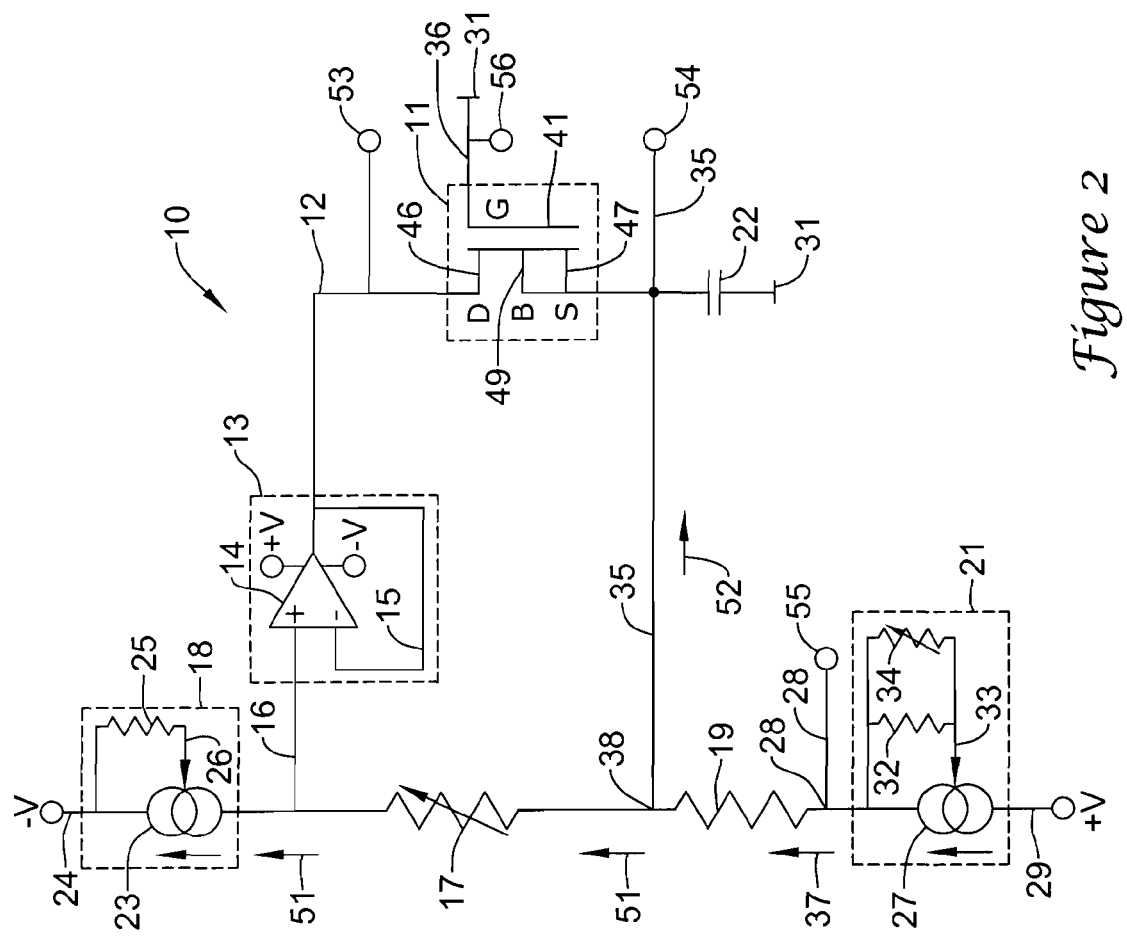
FIG. 2 is a more detailed diagram of the sensor of FIG. 1.
Figure 4:
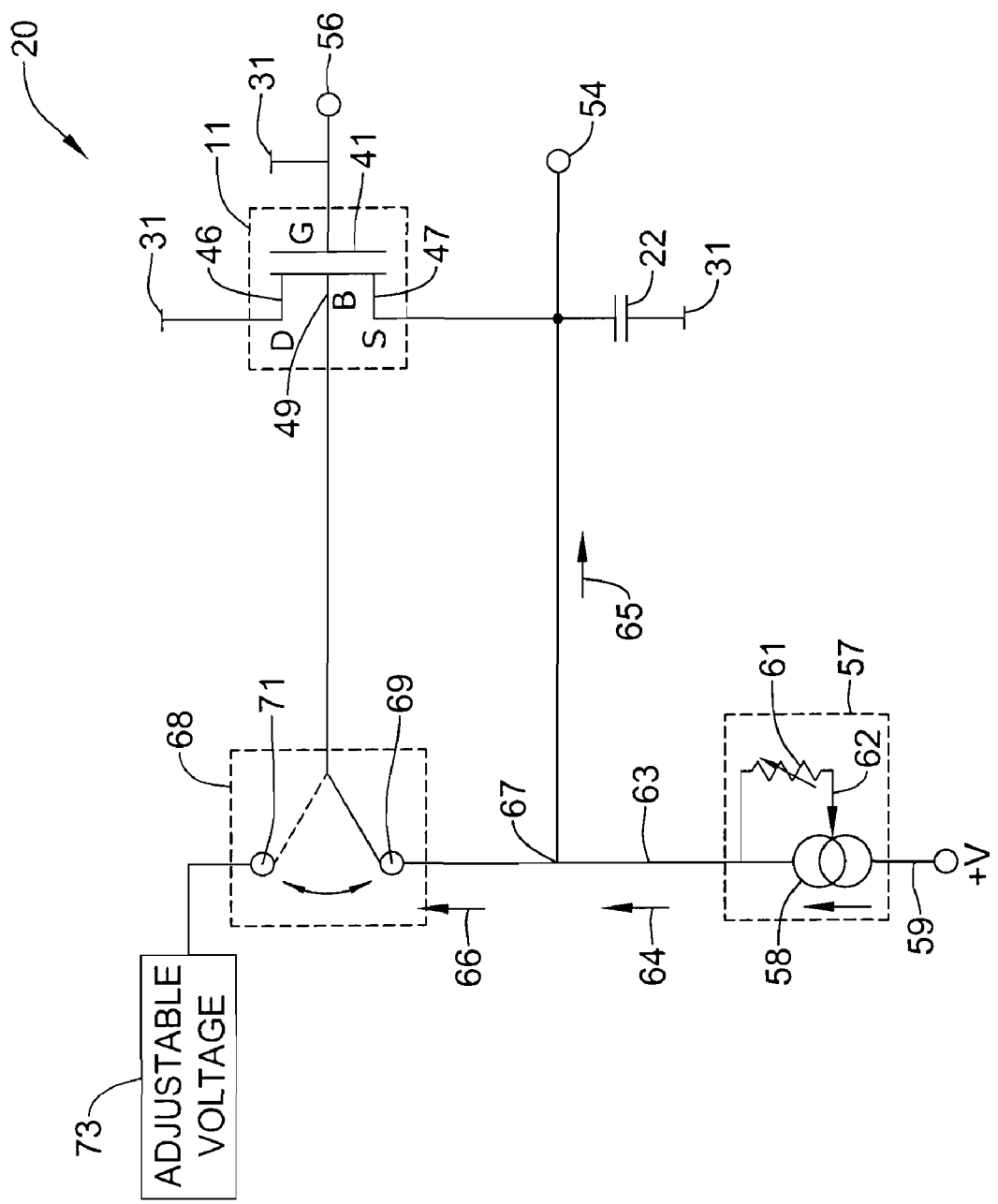
FIG. 4 is a diagram of the sensor incorporating a voltage selection for the bulk of the FET.
Figure 5:
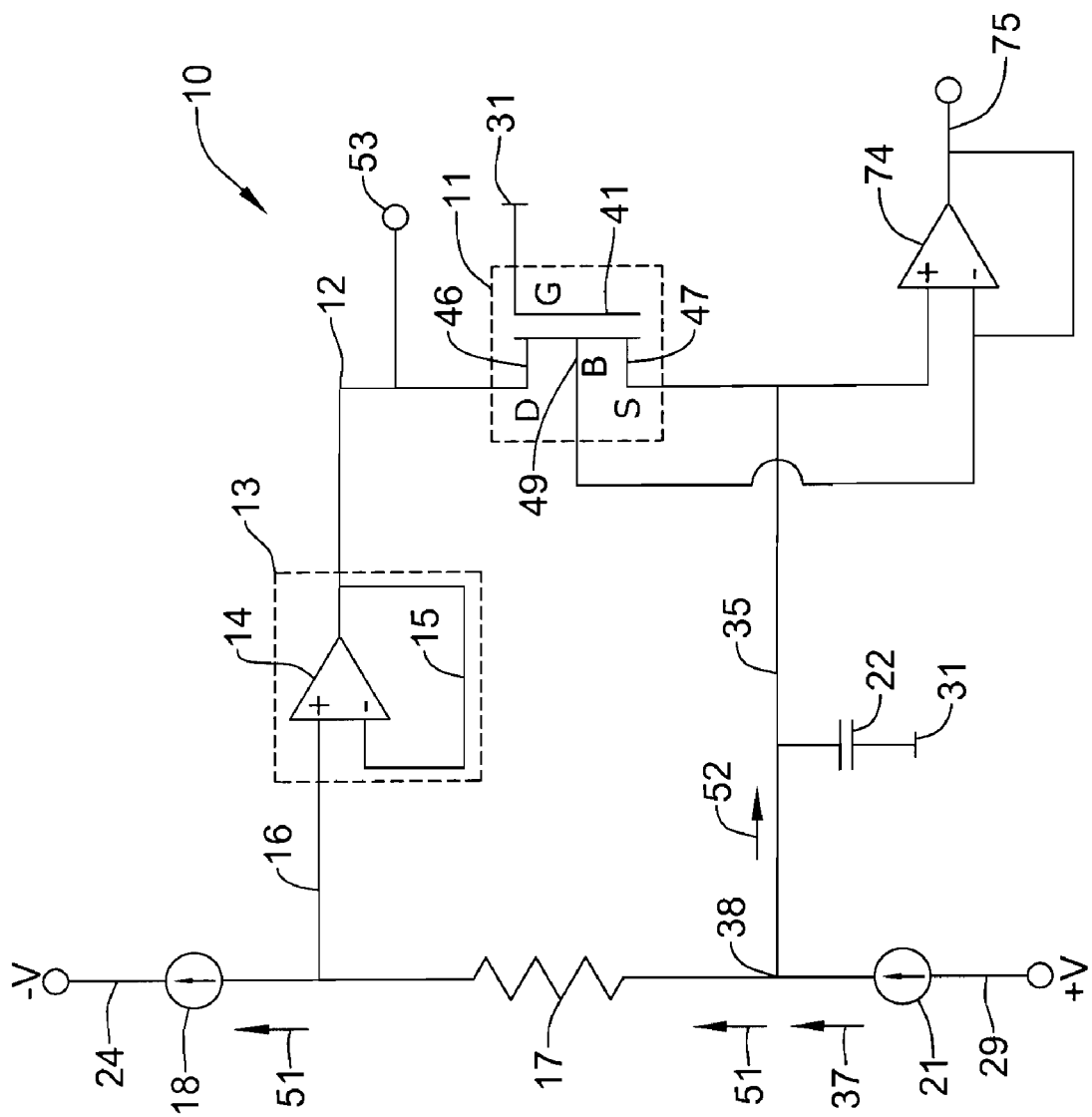
FIG. 5 is a diagram of FET gas sensor incorporating a guard ring for the drain and source of the FET.

The addition of the stabilizing component is shown in FIGS. 1, 2, 4 and 5, such as a capacitor between the FET source and a voltage reference or ground. (Instead of the reference voltage or ground, a variable voltage could be chosen to test the relaxation behavior of the sensor signal.) In FIGS. 1, 2 and 5, the component may be a capacitor of about 14 microfarads (μF), or other appropriate value, may be inserted; and in FIG. 4, there may be an addition of a component such as a capacitor indicated having a value appropriate to the design. It should be noted that in the case of FETs for conducting liquids (ISFETs and so forth), such a component, i.e., a capacitor, may be automatically created by the thin separation between the liquid and the bulk (B) of the FET since the liquid may act a capacitor electrode. The present invention may be different from the liquid-type arrangement in that the present approach may be a gas sensor with low-conductivity gate, which could provide noisy measurements.

FIG. 1 is a diagram of a sensor system 10 for detection and measurement of pH in a solution. Such measurement may be inferred. FIG. 2 is a diagram of the system 10 of FIG. 1, but having an adjustable resistor 17 for determining or setting the voltage across the FET 11. The sensor 10 of FIG. 2 may also have a resistor 19 between the current source 21 and the source 47 of the FET for possibly measuring the current from source 21. More details of current sources 18 and 21 are shown as an example of adjustable sources which may useful with the circuit. Other kinds of current sources may be implemented.

The sensory aspect of system 10 may include a specially designed FET 11. FET 11 may be a P-channel device having a current flow going through from a source to a drain of the FET. (The circuit may alternatively be designed for an N-channel FET.) Drain 46 of the P-channel FET 11 may be connected to an output 12 of a unity gain buffer amplifier module 13. Unity gain buffer amplifier module may have an operational amplifier 14 with an inverting input connected to its output at line 15. Amplifier 14 may be a TL082ACD general purpose J-FET operational amplifier incorporating matched high voltage J-FET and bipolar transistors in a monolithic integrated circuit. Amplifier 14 may be available from STMicroelectronics. A non-inverting input of amplifier 14 may be regarded as an input on line 16 of the unity gain buffer device module 13. Module 13 may be regarded as voltage follower which provides a voltage at the output 12 that essentially is a replica of the voltage at the input from line 16.

Line 16 may be connected to one end of an adjustable resistor 17 and a current source module 18. The other end of the resistor 17 may be connected to the source and bulk of FET 11 and to one end of a resistor 19 in FIG. 2. The other end of resistor 19 may be connected to a current source module 21. A capacitor 22 may be connected between source 47 of FET 11 and a system ground 31. The system ground 31 may be referred to as a reference voltage terminal, reference terminal, or other like term.

Capacitor 22 may be connected close to the FET 11 with no electrical device between capacitor 22 and the FET. The proximity of the capacitor 22 and the sensor FET 11 may be so close such that there is no basis for other noise. A value of the capacitor 22 may be selected to be about 14 μF; however, other values may be considered and used. Noise of the FET 11 sensor may be reduced or eliminated at the originator of the noise. The capacitor 22 may be placed on the same chip of the FET 11. The capacitor or other component in conjunction with FET 11 may effectively amount to a low pass filter, for instance, of signals at an output element of FET 11. The buffer module 13, where the measurements may be taken or recorded from the FET 11 sensor, without filtering, could result in undefined voltage levels. The noise may be so large that the output would not be linear relative to the signals indicating a measurement of a gas parameter.

A lower cutoff may result in a better filter. A value (e.g., 14 μF) of capacitor 22 is may be of concern to the extent of maintaining signals of interest. Also, there may be no reason to increase the value of capacitor 22 beyond a certain value if measuring at a slower rate is desired. The noise reduction may generally be at its best with 14 or so μF. An inherent capacitance value may accommodate a particular resistance of the FET 11 gate, which may be distributed over an area of the gate, resulting in a certain gate time constant.

Current source module 18 may include a constant current source 23 connected to line or terminal 16 at one end. The other end or terminal 24 of source 23 may be connected to a minus voltage source supply. Current source 23 may be a three-terminal adjustable current source LM234Z-6. It may be available from National Semiconductor. A resistor 25 may be connected between terminal 24 and a terminal 26 of current source 23. A value of resistor 25 may set the amount of the current entering and leaving source module 18. An example is a 250 ohm resistor 18 that may cause a current flow through into source module 18 of about 0.27 milliamps (mA).

Similarly, current source module 21 may include a constant current source 27 having a terminal 28 connected to the other end of resistor 19 and a terminal 29 connected to a positive voltage source supply. Current source 27 may be a three-terminal adjustable current source LM234Z-6 as in source module 18. A resistor 32 may be connected between the terminal 28 and terminal 33 of current source 27. The value of resistor 32 may set the amount of current going through source module 21. Another resistor 34 may be connected in parallel with resistor 32. Resistor 34 may be adjusted so that the amount of current from the current source 27 may be changed to a desired amount. The amount of current may be calculated as $$I = V \times ((1/R_1) + (1/R_2)),$$

where V is the voltage across the terminals of module 21, $R_1$ is the value of resistor 32 in ohms and $R_2$ is value of resistor 34 in ohms. This formula may also be applicable to current source module 18.

Figure 3:
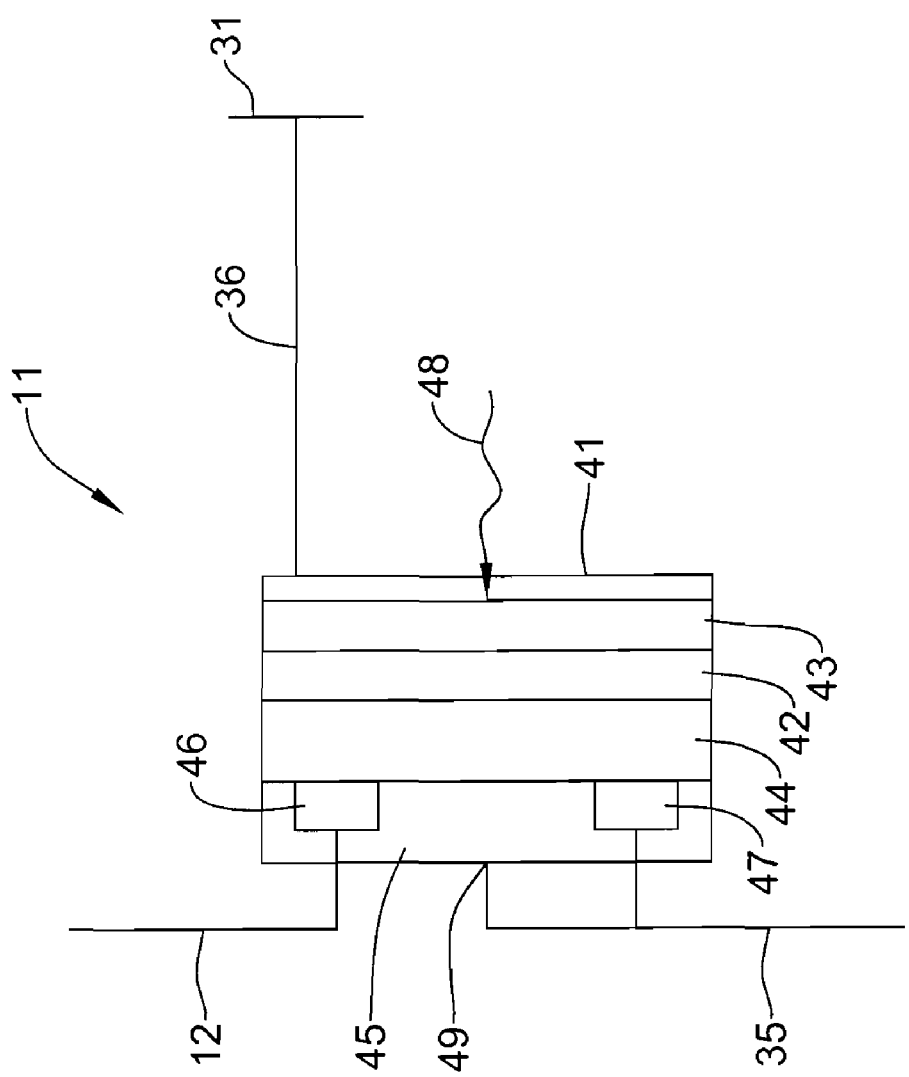
FIG. 3 is a diagram of the FET of the sensor.

FIG. 3 shows additional detail of FET 11 as it relates to gas sensing. FET 11 may be a pH sensitive device like a liquid ISFET sensor but does not use the test liquid as its gate. A gate may be a conductive part of a layer 41 which is a thin conductive polymer having a thickness in a range between 10 and 100 nanometers (nm). An example thickness of the polymer may be about 40 nm. An instance of a conductive polymer may be polypyrrole. There may be a layer 42 of $Ta_2O_5$ proximate to layer 41. An interface layer 43 may be situated between layers 41 and 42. There may be a layer 44 of $SiO_2$ proximate to layer 42. A layer 45 of Si may be proximate to layer 44. Also, there may be a drain 46 and a source 47 situated in layer 45 and proximate to layer 44. Drain 46 may be connected to conducting line 12. Source 47 may be connected to conducting line 35. Also, line 35 may be connected to a bulk 49 of a body, substrate or silicon layer 45.

The layer 41 of the conductive polymer may be a spin coating for purposes of obtaining thinness of the layer. The polymer may be doped with a strong acid. An example may be a sulfonated organic acid. The acid may stay in the polymer but has a strong acidic function. Various kinds of acids may be used for doping the polymer. The acid may push protons into the $Ta_2O_5$ layer 42. There may be a certain charge distribution without a target gas. Ammonia, for instance, may be a target gas 48. An alkaline gas 48 may take away some of protons pushed into the $Ta_2O_5$ layer 42, in that some of the protons may flow back from the $Ta_2O_5$ to the polymer in a form of $NH_4^+$ ions. In other words, the ammonia may suck up the protons. A Nernstian or sub-Nernstian response may occur. The fewer protons in the $Ta_2O_5$ may be indicated by a change relative to the gate voltage. This change may be relative to ground 31 in the circuit of FIG. 4 since the drain electrode is grounded. This voltage may be measured at the drain electrode 46 in the circuit of FIG. 2 since the gate electrode 41 is grounded via line 36 to reference terminal 31. The voltage measurement may indicate a concentration of ammonia detected. The concentration of ammonia may have a range about between 10 ppm to 50 ppm. An alarm level of a presence of ammonia may be about 35 ppm. The present FET 11 sensor configuration may be used to detect and measure other gases. Since the gate 41 is not of a plain metal such as Pd as may be the case in a conventional hydrogen sensitive FET, the gate may have low conductivity and a voltage indicating a presence of a target gas 48, rather than a liquid, may have some noise. Thus, a capacitor 22 may be connected close to an electrode such as a source 47 of the FET 11 and to ground or reference terminal 31. On the other hand, with a conductive liquid sensor (e.g., an ISFET), and having the liquid as a gate of the transistor, a capacitor may be inherently present there for sensor signal filtering.

Relative to the sensor 10 circuit of FIG. 2, a current 37 may flow from current source module 21 along line 28 through resistor 19. The current 37 may split after resistor 19 at a node 38 into currents 51 and 52. Current 51 may flow through the adjustable resistor 17, which presents a voltage $V_{sd}$ across the source 47 and drain 46 of FET 11. Current 51 may flow through current source module 18. The amount of current that may be diverted to the non-inverting input of unity gain buffer module 13 is negligible. Buffer module 13 may present approximately the same voltage at the end of resistor 17 connected to current source module 18 as on line 12 connected to the drain electrode 46 of FET 11.

Current 52 may flow along conducting line 35 to FET 11. Line 35 may be connected to the source 47 and bulk 49 terminals of FET 11. Also, line 35 may connect filter capacitor 22 to source 47. Virtually all of the current 52 goes through FET 11 to line 12. The current at unity buffer 13 may go to or be from the power supplies (V+, V−) connected to amplifier 14.

Voltages $V_d$, $V_s$ and $V_i$ relative to system or reference ground 31 may be measured at terminals 53, 54 and 55, respectively. Terminals 53, 54 and 55 may ultimately be connected to drain 46, source 47, and the output of current source module 21 via lines 12, 35 and 28, respectively. Since line 36 connects gate 41 to ground 31, $V_g$ on terminal 56, which is connected to gate 41 via conductive line 36, may be regarded as being at zero volts, except it may instead be temporarily connected to a signal generator for testing the sensing system 10 circuit. It may be noted that $V_s - V_d = V_{sd}$ and $V_i - V_s = I_{37} \times R_{19} + I_{51} \times R_{17}$, where $I_{37}$ is the value of current 37, $R_{19}$ is the value of resistor 19, $I_{51}$ is the value of current 51, and $R_{17}$ is the value of resistor 17. $V_d$ at terminal 53 may be regarded as the sensor signal indicating a presence of a detected target gas 48

Resistor 19 may be removed as its presence is primarily for current and/or voltage measurements and possible adjustments in a test or laboratory environment. Resistor 17 may be set to attain a desired $V_{sd}$ for optimal sensor 10 operation.

FIG. 1 is an elementary schematic of the sensor 10 circuit. The basic current source modules 18 and 29 are shown and the test resistor 19 is absent. The circuit of sensor system 10 may keep current going from the source to the drain at a constant current 52 and keep the $V_{sd}$ constant at current 51 times the resistor 17 value. The $V_d$, which is the signal voltage may be measured and plotted as either $V_{dg}$ (where g may be the gate) or $V_{sg}$ which is equal to $V_d - V_{sd}$.

The capacitor 22 may be intended for use with a highly resistive gate 41, such as: thin semiconducting films, e.g., thinner than 100 nm; very thin films of conducting materials in many islands; or even only a surface with some surface conductivity, surrounded by a guard ring. Another application may be in a low-conductivity fluid. The influence of a highly resistive gate might be represented in the circuit by a large resistor (not shown) inserted between gate 41 and ground 31. Then, one might assume that the gate 41 cannot control oscillations of $V_{dg}$ (drain 46 to gate 41 voltage) which have a time constant greater than $\tau_g$ which is a product of a gate resistance G and a gate capacitance G (not shown). Capacitance G may be the capacitance between gate 41 and the rest of FET 11.

With T equal to the transconductance of the FET 11, capacitor 22 may act like a low-pass filter for signal voltage $V_d$, with a time constant, $\tau_f$ (tau sub f), which is about equal to the capacitance of capacitor 22 divided by T. This equality might be confirmable by measurements to within five percent.

$\tau_f$ (tau sub f) may, for instance, be hypothetically assumed as significantly larger than $\tau_g$ (tau sub g). That is, the capacitance of capacitor 22 divided by T is significantly greater (>>) than the resistance G multiplied by capacitance G; or the resistance G is significantly less (<<) than the capacitance of capacitor 22 divided by the product of capacitance G and the inverse of T, giving an upper limit for resistance G. This may mean that if gate 41 becomes too resistive, then the circuit of system 10 no longer can effectively control FET 11. Stating this in other words or terms, t(f) should be significantly larger than t(G), i.e., C(f)/T>>R(G)*C(FET) or, equivalently, R(G) <<C(f)/C(FET)*(1/T), giving an upper limit for R(G), that is, if the gate becomes too resistive, the circuit no longer can control the FET effectively.

FIG. 4 shows a schematic of a circuit of an alternative FET-based gas sensor system 20. A current source 57 module may have a current source 58 with a connection 59 connected to a positive voltage supply (+V). Current source 58 may be a three terminal adjustable source LM134. An adjustable resistor 61 may have one end connected to a terminal or conductive line 63 of module 57 which is connected to current source 58, and another end connected to a terminal 62 of the current source 58 for purposes of adjusting a constant current 64 from source 58 and module 57. Adjustable resistor 61 may replaced with a fixed resistor having an appropriate resistance value for a desired amount of current 64.

Current 64 may go to a node 67 and be split into currents 65 and 66 when switch 68 connects bulk 49 of transistor 11 to terminal 69. However, current 66 may be negligible. If switch 68 connects bulk 49 to terminal 71, then terminal 69 may be an open circuit with current 66 being virtually zero. One may assume for present purposes that current 65 is equal to current 64.

Current 65 may proceed to source 47 of FET 11, proceed on to drain 46 and to a reference terminal or ground 31. The bulk 49 voltage $V_B$ may be set at a voltage of source 47 which may be regarded as a sensor signal or voltage $V_s$ at terminal 54, or be set at a voltage fixed above $V_s$ (i.e., $V_B \geq V_s$. Switch 68 may be set to terminal 69 for $V_B = V_s$ or to terminal 71 for $V_B > V_s$. With switch 68 connecting bulk 49 to terminal 71, terminal 71 may be connected to an output of a unity buffer amplifier (not shown but like amplifier 13 of FIG. 1) with the input connected to terminal 69. Alternatively, with switch 68 in the same position, terminal 71 may be connected to an adjustable voltage module 73. Module 73 may be one of various examples of adjustable voltage sources or terminals. One example of module 73 circuitry may include a wiper terminal of a potentiometer which may be a resistance connected between a +V supply terminal and a ground or reference voltage terminal. The potentiometer may effectively be a voltage divider where terminal may be moved so that a voltage between zero and +V may be selected.

The voltage provided to terminal 71 may be greater than $V_s$ at terminal 54. Gate 41 may be connected to ground or reference voltage terminal 31. However, for testing purposes, gate 41 may be temporarily connected to a signal generator that puts out, for example, a low voltage square wave signal. A resulting output from the FET 11 may be a square wave that has a sloping edge revealing a time constant of the circuit component 22 and the FET 11.

The structure and operation of FET 11 in FIG. 5 appear essentially the same as FET 11 described relative to FIGS. 1-3 herein, except that drain 46 may be connected to the reference terminal 31 and the sensor signal may be monitored at source 47 via terminal 54. Filter 22 may be connected across source 47 and the ground or reference terminal 31. Filter 22 may, as noted relative to FIGS. 1-3, significantly reduce noise without detrimentally reducing the sensor or detection signal of a target gas.

FIG. 5 is a circuit of the present sensor 10 like that in FIG. 1 except for another operational amplifier 74 which may be used as a guard ring for the drain 46 and source 47 of FET 11. An output 75 of the amplifier 74 may be used to connect the bulk 49 or other guard ring to prevent leakage currents to the source 47 and drain 46. The non-inverting input of amplifier 74 may be connected to source 47. The output 75 may also be connected to the inverting input of amplifier 74 as well as to bulk 49. As in other diagrams of the present invention, a filter 22 may be connected between source 47 and reference terminal or ground 31. Filter 22 may be a capacitor of about 14 microfarads.

Figure 6:
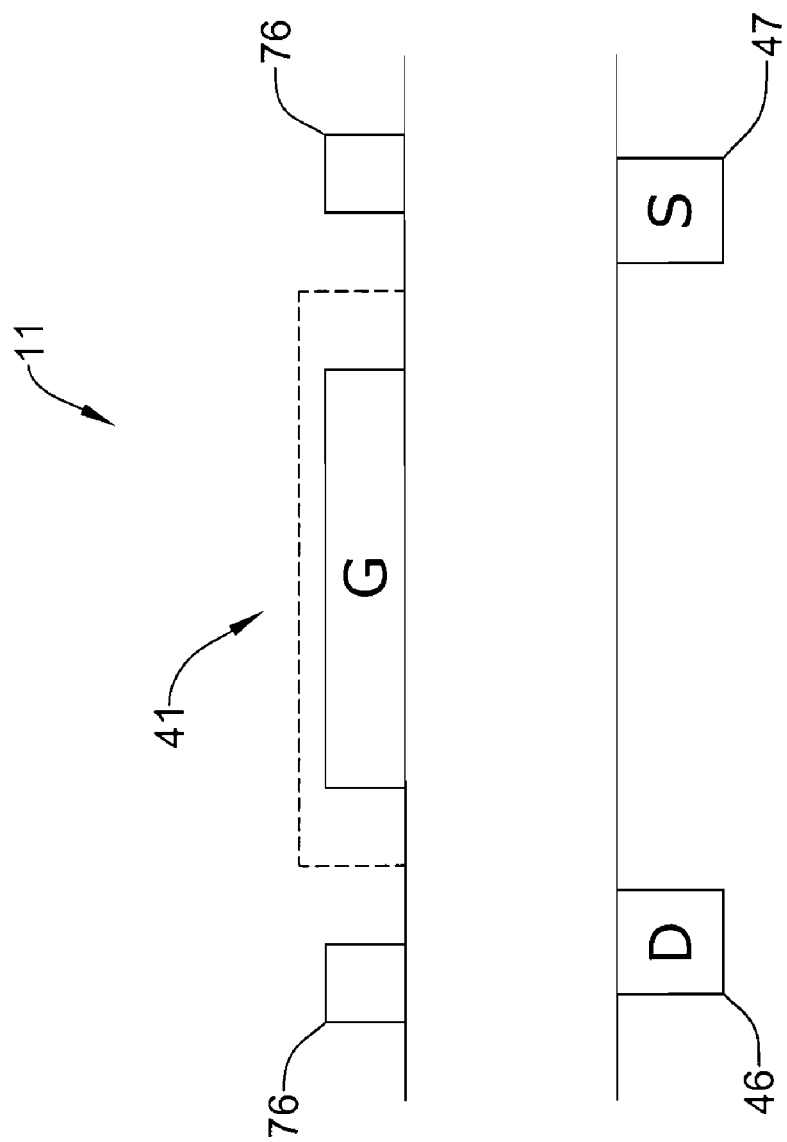
FIG. 6 is a diagram of a guard ring on the FET.

FIG. 6 is a diagram of a side cutaway view of FET 11 having the gate 41, drain 47 and drain 46. Also shown is a guard ring 76 around the FET. The guard ring 76 may or may not be connected to a voltage terminal. The material of ring 76 may be aluminum or other appropriate conductor.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A sensor comprising:
a FET for sensing a low conductivity fluid;
a first circuit component connected to the FET;
an amplifier having an output connected to a drain of the FET; and
a second circuit component connected between a source of the FET and an input of the amplifier; and
wherein:
the first circuit component and the FET are for providing filtering of FET signals of sensing;
the FET comprises a resistive gate; and
the first circuit component is connected between the source of the FET and a reference voltage terminal.

2. The sensor of claim 1, wherein:
the first circuit component is a capacitor; and
the second circuit component is a resistor.

3. The sensor of claim 2, wherein:
the input of the amplifier is a non-inverting input; and
an inverting input of the buffer amplifier is connected to the output of the amplifier.

4. The sensor of claim 3, further comprising a first current source connected to the source of the FET.

5. The sensor of claim 4, further comprising a second current source connected to the non-inverting input of the amplifier.

6. The sensor of claim 1, wherein the FET further comprises a guard ring.

7. A fluid sensor system comprising:
a FET sensor having a gate of conductivity;
a capacitive component having a first end connected to a source of the FET, and a second end connected to a reference terminal;
a first buffer amplifier having an output connected to a drain of the FET;
a resistive component having a first end connected to the source of the FET and having a second end connected to an input of the first buffer amplifier; and
a second buffer amplifier having an input connected to the source of the FET and an output connected to a bulk of the FET.

8. The system of claim 7, further comprising a first current source connected to the first end of the resistive component.

9. The system of claim 8, further comprising a second current source connected to the second end of the resistive component.

10. A sensor comprising:
a FET for sensing a low conductivity fluid; and
a first circuit component connected to the FET; and
wherein:
the first circuit component is a capacitor;
the first circuit component and the FET are for providing filtering of FET signals of sensing;
the FET comprises a resistive gate; and
the first circuit component is connected between a source of the FET and a reference voltage terminal.

11. The sensor of claim 10, further comprising:
an amplifier having an output connected to a drain of the FET; and
a second circuit component connected between the source of the FET and an input of the amplifier.

12. The sensor of claim 11, wherein:
the second circuit component is a resistor.

13. The sensor of claim 11, wherein:
the input of the amplifier is a non-inverting input; and
an inverting input of the buffer amplifier is connected to the output of the amplifier.

14. The sensor of claim 13 further comprising a first current source connected to the source of the FET.

15. The sensor of claim 14, further comprising a second current source connected to the non-inverting input of the amplifier.

16. The sensor of claim 10, wherein the FET further comprises a guard ring.

* * * * *